United States Patent [19]

Brooks

[11] Patent Number: 5,780,489

[45] Date of Patent: Jul. 14, 1998

[54] METHOD FOR TREATING AMYOTROPHIC LATERAL SCLEROSIS

[76] Inventor: Benjamin Rix Brooks, 4818 Fond Du Lac Trail, Madison, Wis. 53705

[21] Appl. No.: 697,157

[22] Filed: Aug. 21, 1996

[51] Int. Cl.$^6$ .................................................. A01N 43/78
[52] U.S. Cl. ......................................... 514/369; 514/550
[58] Field of Search ................................. 514/550, 369

[56] References Cited

U.S. PATENT DOCUMENTS

| | | |
|---|---|---|
| 4,335,210 | 6/1982 | Meister et al. . |
| 4,434,158 | 2/1984 | Meister et al. . |
| 4,438,124 | 3/1984 | Meister et al. . |
| 4,647,571 | 3/1987 | Meister et al. . |
| 4,665,082 | 5/1987 | Meister et al. . |
| 4,879,370 | 11/1989 | Meister . |
| 5,093,478 | 3/1992 | Griffith et al. . |
| 5,208,249 | 5/1993 | Rowe et al. . |
| 5,403,861 | 4/1995 | Goldin et al. .......................... 514/634 |
| 5,447,712 | 9/1995 | White et al. . |
| 5,464,825 | 11/1995 | Anderson et al. . |

FOREIGN PATENT DOCUMENTS 0 204 589  12/1986  European Pat. Off. .

OTHER PUBLICATIONS

Anderson et al., 1985, "Glutathione Monoethyl Ester: Preparation, Uptake by Tissues, and Conversion to Glutathione", Arch. Biochem. Biophys. 239:538–548.

Anderson and Meister, 1989, "Marked Increase of Cysteine Levels in Many Regions of the Brain After Administration of 2–Oxothiazolidine–4–Carboxylate", FASEB J. 3:1632–1636.

Bensimon et al., 1994, "A Controlled Trial of Riluzole in Amyotrophic Lateral Sclerosis", N. Eng. J. Med. 330:585–591.

Bernard et al., 1984, "Effect of N–Acetylcysteine on the Pulmonary Response to Endotoxin in the Awake Sheep and upon In Vitro Granulocyte Function", J. Clin. Invest. 73:1772–1784.

Borchelt et al., 1995, "Superoxide Dismutase 1 Subunits with Mutations Linked to Familial Amyotrophic Lateral Sclerosis Do Not Affect WIId–Type Subunit Function", J. Biol. Chem. 270:3234–3238.

Bowling et al., 1993, "Superoxide Dismutase Activity, Oxidative Damage and Mitochondrial Energy Metabolism in Familial and Sporadic–Amyotrophic Lateral Sclerosis", J. Neurochem. 61:2322–2325.

Deng et al., "Amyotrophic Lateral Sclerosis and Structural Defects in Cu,Zn Superoxide Dismutase", Science 261:1047–1051.

Levy et al., 1993, "Transport of Glutathione Diethyl Ester into Human Cells", Proc. Natl. Acad. Sci USA 90:9171–9175.

Louwerse et al., 1995, "Randomized, Double–Blind, Controlled Trial of Acetylcysteine in Amyotrophic Lateral Sclerosis", Arch. Neurol. 52:559–564.

Meister and Anderson, 1983, "Glutathione", Ann. Rev. Biochem. 52:711–760.

Meister et al., 1986, "Intracellular Cysteine and Glutathione Delivery Systems", J. Am. Coll. Nutr. 5:137–151.

Mesina et al., 1989, "Administration of L–2–Oxothiazolidine–4–Carboxylate Increases Glutathione Levels in Rat Brain", Brain Res. 478:181–183.

Olsson et al., 1988, "Pharmacokinetics and Bioavailability of Reduced and Oxidized N–Acetylcysteine", Eur. J. Pharmacol. 34:77–82.

Puri and Meister, 1983, "Transport of Glutathione, as γ–Glutamylcysteinylglycyl Ester, Into Liver and Kidney", Proc. Natl. Acad. Sci. USA 80:5258–5260.

Rosen et al., 1993, "Mutations in Cu/Zn Superoxide Dismutase Gene are Associated with Familial Amyotrophic Lateral Sclerosis", Nature 362:59–62.

Rothstein et al., 1992, "Decreased Glutamate Transport by the Brain and Spinal Cord in Amyotrophic Lateral Sclerosis", N. Eng. J. Med. 326:1464–1468.

Rothstein et al., "Chronic Inhibition of Glutamate Uptake Produces a Model of Slow Neurotoxicity", Proc. Natl. Acad. Sci. USA 90:6591–6595.

Rothstein et al., 1994, "Chronic Inhibition of Superoxide Dismutase Produces Apoptotic Death of Spinal Neurons", Proc. Natl. Acad. Sci. USA 91:4155–4159.

Shikama et al., 1995, "Transport and Metabolism of Glutathione Isoproply Ester in Cerebrospinal Fluid", Res. Comm. in Mol. Pathol. and Pharmacol. 88:349–357.

Taylor et al., 1992, "Elevation of Lung Glutathione by Oral Supplementation of L–2–Oxythiazolidine–4–Carboxylate Protects Against Oxygen Toxicity in Protein–Energy Malnourished Rats", FASEB J. 6:3101–3107.

Tsan et al., 1989, "Modulation of Endothelial GSH Concentrations: Effect of Exogenous GSH and GSH Monoethyl Ester", J. Appl. Physiol. 66:1029–1034.

Williamson and Meister, 1981, "Stimulation of Hepatic Glutathione Formation by Administration of L–2–Oxythiazolidine–4–Carboxylate, a 5–Oxo–L–Prolinase Substrate", Proc. Natl. Acad. Sci. USA 78:936–939.

Williamson et al., 1982, "Intracellular Cysteine Delivery System that Protects Against Toxicity by Promoting Glutathione Synthesis", Proc. Natl. Acad. Sci. USA 79:6246–6249.

Applied Genetic News, "ALS treated with glutathione booster", vol. 16, No. 9, p. 9, Dec. 1995.

Kalayjian et al., "A phase I/II trial of intraveneous L–2–oxothiazolidine–4–carboxylic acid (procysteine) in asymptomatic HIV–infected subjects", J. Acquir Immune Defic Syndr, vol. 7, No. 4, pp. 369–374, Apr. 1994.

Minhas et al., "Comparison of the delivery of reduced glutathione into P388D cells by reduced glutathione and its mono–and diethyl ester derivatives", Biochemical Pharmacology 1995, vol. 49, pp. 1475–1482, 1995.

Stedman's Medical Dictionary, 24th ed., Williams & Wilkins, Baltimore, p. 1264, 1982.

*Primary Examiner*—Michael P. Woodward
*Assistant Examiner*—Brenda G. Brumback
*Attorney, Agent, or Firm*—Pennie & Edmonds LLP

[57] ABSTRACT

The invention provides a method for treating amyotrophic lateral sclerosis in a patient which comprises administering to the patient an effective amount of a non-cysteine glutathione precursor or a glutathione derivative so as to increase the intracellular glutathione levels and alleviate a symptom of amyotrophic lateral sclerosis. The non-cysteine substrate may be a thiazolidine-4-carboxylate analog, a thiazolidine-4-carboxylate analogs ester, or a pharmaceutically acceptable salt thereof.

22 Claims, No Drawings

METHOD FOR TREATING AMYOTROPHIC LATERAL SCLEROSIS

1. INTRODUCTION

The present invention relates to a method for the treatment of amyotrophic lateral sclerosis (ALS). In particular, it relates to the use of either glutathione (GSH) derivatives such as glutathione alkyl monoesters or glutathione diesters or non-cysteine glutathione precursors to increase intracellular GSH levels in neurons, particularly motor neurons. GSH derivatives or non-cysteine glutathione precursors protect neurological cells from oxidative damage, thereby preventing, reducing the progression of, alleviating the symptoms of and/or treating ALS. Preferably, the non-cysteine glutathione precursor is a thiazolidine-4-carboxylate analog, such as L-2-oxothiazolidine-4-carboxylate.

2. BACKGROUND OF THE INVENTION

2.1. Clinical Features of ALS

ALS is a progressive degenerative disease of the voluntary motor system (L P Rowland, *Merritt's Textbook of Neurology*, ed. L P Rowland, Hereditary and acquired motor neuron disease (Philadelphia: Williams and Wilkins, 1995)). The clinical course is relentless with a linear decline in strength with time (T L Munsat et al., 1988, *Neurology* 38: 452–458). The prevalence of ALS is 4 to 6 cases per 100,000 with an incidence of 0.4 to 1.8 per 100,000 (W A Horton, R Eldridge, and J A Brody, 1976, "Familial motor neuron disease: evidence for at least three different types," *Neurology* 26: 460–465). The majority of ALS cases are sporadic. However, 10–15% of cases are inherited as an autosomal dominant trait (FALS) (D W Mulder et al., 1986, "Familial adult motor neuron disease: amyotrophic lateral sclerosis," *Neurology* 36: 511–517). The sporadic and FALS forms of ALS are clinically and pathologically identical.

Clinical signs of both lower and upper motor neuron involvement are required for a definitive diagnosis. Symptoms can begin either in bulbar or limb muscles (L P Rowland, 1995). The median age of onset is 55 and the median survival is less than five years. One of the characteristics is the progressive loss of muscle strength. Age and gender are the only risk factors repeatedly documented in epidemiological studies (J F Kurtzke, 1991, "Risk Factors in Amyotrophic Lateral Sclerosis," *Adv Neurol* 56: 245–270). There is a slight male predominance (3:2 male to female ratio) in sporadic ALS. There is no racial or geographic predisposition.

2.2. Pathogenesis and the Free Radical Hypothesis

The cause of sporadic ALS is unknown. Many causes of ALS have been proposed including atypical poliovirus infection, intoxication by exogenous metal-toxins, autoimmune processes targeting motor neurons, cytoskeletal abnormalities, trophic factor deprivation, mitochondrial dysfunction, and toxicity from excess excitation of the motor neuron by transmitters such as glutamate (L P Rowland, "Ten central themes in a decade of ALS research," in *Amyotrophic Lateral Sclerosis and Other Motor Neuron Diseases*, ed. L P Rowland, Advances in Neurology (Raven Press, 1992), 3–23). Given the clinical and epidemiological similarity between sporadic and FALS, it is a reasonable premise that an understanding of the familial disease will illuminate possible pathophysiological mechanisms in sporadic ALS.

In some cases of FALS, genetic studies have established that the primary defects are mutations in the gene for cytosolic, copper-zinc superoxide dismutase (SOD1) (D R Rosen et al., 1993). Currently more than thirty five different mutations in SOD1 have been reported exclusively in FALS. SOD1 is a metalloenzyme of about 153 amino acids that is expressed in all eukaryotic cells. It is one of a family of three SOD enzymes, which include manganese-dependent, mitochondrial SOD (SOD2) and copper/zinc extracellular SOD (SOD3) (I Fridovich, 1986, "Superoxide dismutases," *Advances in Enzymology* 58: 61–97). The primary function of the SOD1 enzyme is believed to be detoxification of the superoxide anion by conversion to hydrogen peroxide (W Huber and M G P Saifer, *Superoxide and Superoxide Dismutase*, ed. A. M. Michaelson, J. M. McCord, and I. Fridovich, Orgotein, the drug version of bovine laboratory animals (New York: Academic Press, 1977). Hydrogen peroxide is subsequently detoxified by glutathione peroxidase or catalase to form water. Superoxide is potentially toxic by itself, and also can produce the more toxic hydroxyl radical either through formation of hydrogen peroxide or by reaction with nitric oxide (W Huber and M G P Saifer, 1977). Superoxide also interacts with nitric oxide and forms peroxynitrite anion which may be directly toxic to cells and also generates hydroxyl radicals (J S Beckman et al., 1992, "Kinetics of superoxide dismutase- and iron-catalyzed nitration of phenolics by peroxynitrite," *Arch. Biochem. Biophys.* 298: 438–445; B Halliwell and O. I Aruoma, *Molecular Biology of Free Radical Scavenging Systems*, ed. J G Scandalios (Cold Spring Harbor, New York: Cold Spring Harbor Laboratory Press, 1992)). An important implication of these biochemical properties of SOD1 is that FALS may arise as a consequence of abnormalities of free radical homeostasis and resulting cellular oxidative stress. More broadly, given the similarities between sporadic and familial ALS, it is a reasonable premise that sporadic ALS may also be a free radical disease.

The effects of the FALS mutations on SOD1 function are not fully understood. Many FALS-associated SOD1 mutations reduce SOD1 activity in tissues such as brain and erythrocytes (H-X Deng et al., 1993, "Amyotrophic lateral sclerosis and structural defects in Cu,Zn superoxide dismutase," *Science* 261: 1047–1051; A C Bowling et al., 1993, "Superoxide dismutase activity, oxidative damage and mitochondrial energy metabolism in familial and sporadic amyotrophic lateral sclerosis," *Journal of Neurochemistry* 61: 2322–2325). In vitro, the mutations appear generally to alter stability of the mutant molecule, shortening the half-lives of the mutant proteins without necessarily reducing the specific activity of the SOD1 molecule (D R Borchelt et al., 1995, "Superoxide dismutase 1 subunits with mutations linked to familial amyotrophic lateral sclerosis do not affect wild-type subunit function," *Journal of Biological Chemistry*, 270, no. 7: 3234–3238). Why these mutations cause neuronal cell death remains problematic. Recently, it has been shown that in chronic organotypic spinal cord cultures, partial reduction of activity of SOD1 by chronic application of SOD1 anti-sense oligonucleotides triggers apoptotic nerve cell death, including fulminant motor neuron death. The death process, in vitro, is reversed by agents which enhance anti-oxidant defenses (e.g. N-acetylcysteine) (J D Rothstein et al., 1994).

However, many lines of evidence argue strongly that the disease arises not from loss of SOD1 function, but rather from an adverse or novel property of the mutant SOD1 molecule. Dominantly inherited diseases, like FALS, are thought to arise because a single mutant allele produces a mutant protein with a novel property that is, in some way, toxic to the cell. Several laboratories have now demonstrated that mice which over-express high levels of mutant SOD1 protein develop a lethal, denervating, paralytic disease that resembles ALS clinically and pathologically (M E Gurney et al., 1994, "Motor neuron degeneration in mice that express a human Cu, Zn superoxide dismutase mutation," *Science* 264: 1772–1775; D L Price, D W Cleveland, and V E Koliatosos, 1994, "Motor neuron disease and animal models," *Neurobiol. Disease* 1: 3–11). These findings support the hypothesis that the primary effect of the SOD1 mutations is a gain of a toxic function. The molecular mechanisms for this acquired adverse function is not known. If indeed the primary cause of the disease is oxidative cytotoxicity, the gained function presumable involves aberrant production or trafficking of one or more toxic oxidative intermediates.

2.3. Endogenous Antioxidant Activity and Indirect Measures of Free Radical Activity Levels of free radicals are regulated by two major endogenous antioxidant systems: non-enzymatic free radical scavengers (vitamins E and C, beta-carotene, and uric acid) and enzymes (SOD, catalase, and glutathione peroxidase) (B Halliwell and O. I Aruoma, 1992: V L Dawson et al., 1993, "Mechanisms of nitric oxide-mediated neurotoxicity in primary brain cultures," *Journal of Neurosciences* 13:2651–2661). Reactive oxygen species are highly reactive and typically short-lived. It is difficult to measure their levels directly. Accordingly, several biochemical parameters are used to gauge the extent of oxidative damage to various cellular constituents, including markers of oxidative damage to DNA, proteins and lipids. Protein oxidation can be quantitated by measuring protein carbonyl groups in plasma and in tissue (B Halliwell and O. I Aruoma, 1992; R A Floyd and J M Carney, 1992, "Free Radical Damage to Protein and DNA: Mechanisms Involved and Relevant Observations on Brain Undergoing Oxidative Stress," *Ann Neurol* 32: S22–S27). Protein carbonyl groups have been found to be increased in brains and spinal cords from sporadic ALS patients as compared to controls and patients with FALS (A C Bowling et al., 1993).

2.4. Pathogenesis and the Glutamate Toxicity Hypotheses

Several lines of evidence suggest a role for glutamate, the primary excitatory neurotransmitter in the central nervous system in the pathogenesis of ALS. These include: (1) the presence of elevated levels of glutamate in cerebrospinal fluid and brain in some cases of sporadic ALS (J D Rothstein et al., 1992), (2) decreased high-affinity glutamate uptake by synaptosomes prepared from spinal cord and motor cones from subjects with ALS (J D Rothstein et al., 1993), (3) decrease expression of the primarily glial GLT-1 glutamate transporter in some cases of sporadic ALS (J D Rothstein et al., 1995, "Selective loss of glial glutamate transporter GLT-1 in amyotrophic lateral sclerosis," *Ann Neurol* 38: 73–84), and (4) prolongation of survival of ALS patients treated with Riluzole, a glutamate release inhibitor, by 12% (G Bensimon et al., 1994).

It is now thought that the motor neuron death process in ALS reflects a complex interplay between oxidative injury, excitotoxic stimulation of the motor neurons, and dysfunction of mitochondria and critical proteins such as neurofilaments.

2.5. Glutathione as Cellular Protectant

GSH is a tripeptide (L-γ-glutamyl-L-cysteinylglycine) that is the most abundant thiol in many cell types (Meister and Anderson, 1983, *Ann. Rev. Biochem.* 52:711–760). While GSH is involved in many cellular processes, it has received particular attention as a cellular protectant against free radicals and reactive oxygen species. For example, the reduced form of GSH plays a role in cell protection by reacting with hydrogen peroxide and organic peroxides, harmful byproducts of aerobic respiration. Therefore, GSH may protect cells from oxidative damage and maintain their normal structure and function.

In an effort to reduce cellular toxicity associated with various disease conditions, different methods have been used to elevate intracellular GSH levels. Since L-cysteine is one of the three amino acids in GSH and a shortage of L-cysteine can result in GSH depletion, this amino acid has been used in an attempt to raise the intracellular levels of GSH. However, this approach is unsuccessful because high extracellular levels of cysteine can be toxic, and this compound is not transported efficiently into cells and is oxidized spontaneously at neutral pH (Meister et al., 1986, *J. Am. Coll. Nutr.* 5:137–151). The administration of GSH itself has not led to increased intracellular GSH levels because intact GSH is not transported efficiently into cells (Meister, U.S. Pat. No. 4,879,370).

Recent studies have shown that GSH esters, specifically GSH isopropyl ester provide protection against cellular ischemia (H Shikama et al., 1995, *Res. Comm. in Mol. Pathology and Pharmacology*, 88:349–357). Shikama et al. found that the rates of uptake of GSH and GSH isopropyl ester were the same into rat cerebrospinal fluid (CSF), but only the ester increased the total GSH, i.e., the sum of GSH and GSH ester. Shikama et al. noted that the increase occurs because the GSH isopropyl ester is more stable that GSH in the CSF. They propose that metabolic stability is due to its reduced affinity for a key enzyme in GSH metabolism, γ-glutamyl transpeptidase. In contrast, other workers have observed faster transport of GSH esters across cell membranes than GSH in cultured cell systems (M F Tsan et al., 1989, *J Appl. Physiol,* 66:1029–1034).

The administration of a cysteine "prodrug", L-2-oxothiazolidine-4-carboxylate (OTZ), has been effective in increasing GSH levels in some cell types (Williamson et al., 1981, *Proc. Natl. Acad. Sci. USA* 78:936). Conversion of OTZ, to cysteine requires the enzyme 5-oxoprolinase.

Since GSH can protect some cells against toxic compounds (Puri and Meister, 1983, *Proc. Natl. Acad. Sci. USA* 80:5258), attempts have been made to increase GSH levels in cells. While cysteine and GSH are not efficiently transported into most animal cells, GSH monoethylester is able to enter human cells to result in an increase in GSH levels under the experimental conditions used (Anderson et al., 1985, *Arch. Biochem. Biophys.* 239:538). Levy et al. reported that GSH diethylester was even more efficiently transported into human cells than the monoester to cause an increase of intracellular GSH levels under the experimental conditions used (Levy et al., 1993, *Proc. Natl. Acad. Sci. USA* 90:9171). Although GSH diethylester is readily converted to monoethyl (glycyl) ester in rodent blood plasma by an esterase, such an esterase activity is absent in human plasma. Thus, GSH diester is stable in human blood, and when it enters human cells which have the esterase, it is converted to GSH monoester and subsequently, to GSH.

In a recent study, N-acetylcysteine (NAC), a simple cysteine derivative which acts as an anti-oxidant directly and by augmenting intracellular glutathione levels, showed a trend towards increasing survival in ALS patients (E S Louwerse et al., 1995, "Randomized, double-blind, controlled trial of acetylcysteine in amyotrophic lateral sclerosis," *Arch. Neurol.* 52: 559–564). In contrast, the compounds described herein, are glutathione alkyl esters or glutathione diesters or non-cysteine glutathione precursors. These offer better oral bioavailability and/or penetrance into cells. Specifically, Olsson et al. and others found low bioavailability of NAC in human studies (B Olsson et al., 1988, *Eur. J. Clin. Pharmacol.* 34:77–82).

2.6. Unpredictable Results of OTZ Administration on Rat Brain GSH Levels

Prior workers have found mixed results in studies of the effects of OTZ on GSH levels in rat brains. Mesina and co-workers found that subcutaneous injections of OTZ lead to a statistically significant increase in the level of GSH in rat brains (J E Mesina et al. 1989, *Brain Research* 478:181–183), whereas other workers, Anderson and Meister, have found that OTZ either had no effect or only slightly increased GSH levels (M E Anderson and A Meister, 1989, *The FASEB Journal*, 3: 1632–1636).

3. SUMMARY OF THE INVENTION

The invention provides a method for treating amyotrophic lateral sclerosis in a patient which comprises administering to the patient an effective amount of a non-cysteine glutathione precursor or a glutathione precursor so as to increase the intracellular glutathione levels and alleviate a symptom of amyotrophic lateral sclerosis. The non-cysteine substrate may be a thiazolidine-4-carboxylate analog, a thiazolidine-4-carboxylate analog ester, or a pharmaceutically acceptable salt thereof.

4. DETAILED DESCRIPTION OF THE INVENTION

ALS is a progressive uniformly lethal neurodegenerative disorder for which there is no known effective therapy. Recent genetic and biochemical studies implicate free radical toxicity and glutamate excitotoxicity as possible causes of familial amyotrophic lateral sclerosis (FALS) and sporadic ALS (D R Rosen et al., 1993, "Mutations in Cu/Zn superoxide dismutase gene are associated with familial amyotrophic lateral sclerosis," *Nature* 362: 59–62; J D Rothstein, L J Martin, and R W Kuncl, 1992, "Decreased glutamate transport by the brain and spinal cord in amyotrophic lateral sclerosis," *New England Journal of Medicine* 326: 1464–1468; J D Rothstein et al., 1993, "Chronic inhibition of glutamate uptake produces a model of slow motor neuron toxicity," *Proceedings of the National Academy of Science, USA* 90: 6591–6595; and J D Rothstein et al., 1994, "Chronic inhibition of superoxide dismutase produces apoptotic death of spinal neurons," *Proceedings of the National Academy of Science, USA* 91: 4155–4159). Evidence suggests these two mechanisms may occur in concert. Two studies have recently documented that the glutamate-release antagonist, Riluzole, causes a statistically significant, but small (18%) prolongation of lifespan in patients with ALS (G Bensimon et al., 1994, "A controlled trial of Riluzole in amyotrophic lateral sclerosis," *New England Journal of Medicine* 330, no. 9: 585–591). These findings have recently been documented also in an animal model of ALS. This invention is directed to the reduction of free radical toxicity in the pathogenesis of ALS.

Specifically, the invention provides a method for treating ALS in a patient which comprises administering to the patient an effective amount of a non-cysteine glutathione precursor or a glutathione derivative so as to increase the intracellular glutathione levels and alleviate a symptom of amyotrophic lateral sclerosis. The compounds of this invention act to increase GSH levels both intra-cellular and extra-cellular levels (e.g. CSF) and thereby protect neurons, particularly motor neurons.

The non-cysteine substrate may be a thiazolidine-4-carboxylate analog, a thiazolidine-4-carboxylate analog ester, or a pharmaceutically acceptable salt thereof. Preferably, the non-cysteine substrate is L-2-oxothiazolidine-4-carboxylate, a carboxylate ester or a pharmaceutically acceptable salt thereof.

In one embodiment, the method is performed with a glutathione derivative which may be a glutathione diester or a pharmaceutically acceptable salt thereof. The glutathiones diester may be a glutathione dialkylester or a glutathione diethylester. As used herein, alkyl includes an alkyl group of 1 to 10 carbon atoms which may be straight chain or branched, see sections 4.1 and 4.2 below. Alternatively, the glutathione derivative is a glutathione monoester or a pharmaceutically acceptable salt thereof. The glutathione monoester may be a glutathione monoalkylester or a monoethylester or a glutathione isopropyl ester. The pharmaceutically acceptable salt may be a hydrochloride or a hemihydrosulfate.

In the methods described herein the compounds may be administered orally, intravenously, parenterally, or enterally.

The bases of this invention are that (1) free radical-mediated toxicity has a significant role in the pathogenesis of ALS, and (2) chronic treatment with a glutathione repleting agent, such as OTZ, will slow the progression of the clinical features of ALS. This invention is directed to the use of a glutathione repleting agent, such as OTZ, to slow the progressive deterioration of motor and pulmonary function in patients with ALS. Although Riluzole has a small affect on survival, it is currently considered the "standard" of care in ALS. Therefore, the effect of combination therapy with OTZ and Riluzole is compared with Riluzole alone. This entails a phase II, double-blind, bi-center comparison study of the clinical efficacy of OTZ and Riluzole combination therapy versus Riluzole alone in subjects with ALS.

4.1. Non-Cysteine Glutathione Precursors and Their Synthesis

Pursuant to the present invention any non-cysteine substrate that facilitates intracellular glutathione synthesis can be utilized. Preferably, the method comprises the step of administering an agent chosen from the group consisting of L-2-oxothiazolidine-4-carboxylic acid, L-2-oxothiazolidine-4-carboxylate and glutathione esters. However, other thiazolidine-4-carboxylate analogs that are converted intracellularly to cysteine may be utilized.

L-2-oxothiazolidine-4-carboxylate, in vitro, is subjected to the action of 5-oxo-L-prolinase in the presence of adenosine triphosphate to produce S-carboxyl cysteine. The proposed intermediate, S-carboxyl cysteine is then decarboxylated to produce cysteine. Cysteine is then metabolized to provide glutathione. See, U.S. Pat. Nos. 4,335,210; 4,434,158; 4,438,124; 4,665,082; and 4,647,571 the disclosures of which are incorporated herein by reference.

In a similar manner, esters of the thiazolidine-4-carboxylate analog may be used. The ester may be saturated or unsaturated, straight chain or branched of 1 to 10 carbon atoms. Preferably, the ester is a saturated straight chain alkyl group such as methyl, ethyl, propyl, butyl, pentyl, hexyl, heptyl, octo, nonyl or decyl ester. Alternatively, the esters may be branched alkyl esters such as isopropyl, isobutyl, sec-butyl, tert-butyl or isopentyl. Such esters are disclosed in U.S. Pat. No. 5,208,249 the contents of which are hereby incorporated by reference.

In an embodiment of the invention, the composition of the present invention includes: 5- L-2-oxothiazolidine-4-carboxylate in a phosphate buffer. Additional embodiments include:

a) A buffered (pH 5.5–7.5) 1%–10% L-2-oxothiazolidine-4-carboxylate or glutathione ester aqueous solution.

b) A buffered 1%–10% L-2-oxothiazolidine-4-carboxylate or glutathione ester aqueous solution containing any of the following, alone or in appropriate combinations: amino acids, dextrose or other carbohydrate sources, and lipid emulsions.

c) A vial containing a crystalline or lyophilized non-cysteine glutathione precursor to which appropriate aqueous solutions are added at time of use.

d) A gelatin capsule containing a crystalline or lyophilized non-cysteine glutathione precursor.

e) A pill containing a crystalline or lyophilized non-cysteine glutathione precursor.

f) A liquid elemental, protein hydrolysate, carbohydrate and/or lipid emulsion containing enteral dietary supplement containing a non-cysteine glutathione precursor.

The composition may be administered as an adjunct therapy with other typical therapies for ALS. For example, the FDA approved ALS drug Riluzole, steroids, non-steroid anti-inflammatories, prostaglandin synthesis inhibitors (ibuprofen), mucolytics, tumor necrosis factor antibodies, artificial surfactants (Exosurf, Survanta), hyperoxic and ventilation therapies, and antibiotics can be administered with the present invention.

4.2. GSH Derivatives and Their Synthesis

The GSH derivatives for the practice of this invention include GSH alkyl mono- and diesters. For example, the compound may have the structure:

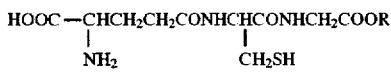

$$HOOC-CHCH_2CH_2CONHCHCONHCH_2COOR$$
$$\phantom{HOOC-C}|\phantom{CH_2CH_2CONHC}|$$
$$\phantom{HOOC-CHC}NH_2\phantom{H_2CONH}CH_2SH$$

wherein R is an alkyl group containing 1 to 10 carbon atoms. Preferably, the methyl and ethyl glutathione esters are used. It is also preferred to use glutathione isopropyl ester. Glutathione esters are disclosed in U.S. Pat. No. 4,784,685, the disclosure of which is incorporated herein by reference. Furthermore, the invention includes N-acetyl and N-acyl GSH mono and diesters. In these compounds the alkyl group is a straight or branched carbon chain having 1 to 10 carbon atoms, preferably 1 to 4 carbon atoms and salts thereof. The GSH alkyl monoester of the invention is esterified at the glycine carboxylic acid group. More specifically, these compounds include GSH monoalkylester hydrochloride, GSH monoester hemihydrosulfate, GSH monoethylester toluenesulfonic acid salt, free base GSH monoesters, monoesters of methanol, ethanol and 2-propanol, and GSH dialkylester hydrochloride. In addition, other GSH derivatives within the scope of the invention include, but are not limited to, N-acyl GSH and N-acyl GSH alkyl mono- and diesters in which the acyl group contains 1 to 9 carbon atoms and can be in a straight or branched chain acyl group such as formyl, acetyl, propyl and isopropyl. These compounds may be prepared by any method well known in the art (Anderson et al., 1985, *Arch. Biochem. Biophys.* 239:538; Levy et al., 1993, *Proc. Natl. Acad. Sci. USA* 90:9171; Meister, U.S. Pat. Nos. 4,879,370 and 5,464,825). The GSH alkyl mono- and diesters may be used as individual species or in combination.

4.3. Formulations

Any suitable route of administration may be employed for providing the patient with an effective dosage of the glutathione esters or non-cysteine glutathione precursors. For example, oral, rectal, parenteral, transdermal, subcutaneous, intramuscular, and the like may be employed as appropriate. Dosage forms include tablets, coated tablets, troches, dispersions, suspensions, solutions, caplets, capsules, patches, and the like.

The pharmaceutical compositions of the present invention comprise glutathione esters or non-cysteine glutathione precursors as active ingredient, or a pharmaceutically acceptable salt thereof, and may also contain a pharmaceutically acceptable carrier, and optionally, other therapeutic ingredients.

The term "pharmaceutically acceptable salts" refers to salts prepared from pharmaceutically acceptable non-toxic acids or bases including inorganic acids and bases and organic acids and bases.

Since the compound of the present invention is both basic and acidic, salts may be prepared from pharmaceutically acceptable non-toxic acids or bases including inorganic and organic acids or inorganic and organic bases. Such salts may contain any of the following anions: acetate, benzensulfonate, benzoate, camphorsulfonate, citrate, fumarate, gluconate, hydrobromide, hydrochloride, lactate, maleate, mandelate, mucate, nitrate, pamoate, phosphate, succinate, sulfate, tartrate and the like. Particularly preferred are benzensulfonate, hydrobromate, hydrochloride and sulfate. Such salts may also contain the following cations: aluminum, calcium, lithium, magnesium, potassium, sodium, zinc, benzathine, chloroprocaine, choline, diethanolamine, ethylenediamine, meglumine, and procaine.

The compositions include compositions suitable for oral, rectal and parenteral (including subcutaneous, intramuscular, and intravenous) administration, although the most suitable route in any given case will depend on the nature and severity of the condition being treated. The most preferred route of the present invention is the oral route. The compositions may be conveniently presented in unit dosage form, and prepared by any of the methods well known in the art of pharmacy.

In the case where an oral composition is employed, a suitable dosage range for use is, e.g., from about 100 mg to about 30 g total daily dose, given as a once daily administration in the morning or in divided doses if required. Preferably, a dose of about 4.5 g to about 21 g is given as a once daily administration. More preferably, a dose range of between about 8 g to about 10 g is given in three divided doses daily. Patients may be upward titrated from below to within this dose range to a satisfactory control of symptoms.

In practical use, glutathione esters or non-cysteine glutathione precursors may be combined as the active ingredient in intimate admixture with a pharmaceutical carrier according to conventional pharmaceutical compounding techniques. The carrier may take a wide variety of forms depending on the form of the preparation desired for administration, e.g., oral or parenteral (including intravenous injections or infusions). In preparing the compositions for oral dosage form any of the usual pharmaceutical media may be employed. Usual pharmaceutical media includes, for example, water, glycols, oils, alcohols, flavoring agents, preservatives, coloring agents, and the like in the case of oral liquid preparations (such as for example, suspensions, solutions, and elixirs); aerosols; or carriers such as starches, sugars, microcrystalline cellulose, diluents, granulating agents, lubricants, binders, disintegrating agents and the like, in the case of oral solid preparations (such as for example, powders, capsules, and tablets) with the oral solid preparations being preferred over the oral liquid preparations. The most preferred oral solid preparation is tablets.

Because of their ease of administration, tablets and capsules represent the most advantageous oral dosage unit form, in which case solid pharmaceutical carriers are employed. If desired, tablets may be coated by standard aqueous or nonaqueous techniques. The parenteral dosage form can consist of a sterile solution of the active ingredient, either in its free or salt form, in physiological buffer or sterile water.

In addition to the common dosage forms set out above, the compounds of the present invention may also be administered by controlled release means and/or delivery devices such as those described in U.S. Pat. Nos. 3,845,770; 3,916, 899; 3,536,809; 3,598,123; 3,630,200; 4,008,719; 4,687,660 and 4,769,207, the disclosures of which are hereby incorporated by reference.

Pharmaceutical compositions of the present invention suitable for oral administration may be presented as discrete units such as capsules, cachets, or tablets, or aerosols sprays, each containing a predetermined amount of the active ingredient, as a powder or granules, or as a solution or a suspension in an aqueous liquid, a non-aqueous liquid, an oil-in-water emulsion, or a water-in oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 100 mg to about 2 g of the active ingredient, and each cachet or capsule contains from about 100 mg to about 2 g of the active ingredient, of the glutathione esters or non-cysteine glutathione precursors. Most preferably, the tablet, cachet or capsule contains either one of two dosages, about 500 mg or about 1 g of the active ingredient.

Some of the preferred formulation are as follows: Each sterile 100 mL glass vial of Procysteine® for injection contains the following ingredients:

| Procysteine ®, 5% injection | |
|---|---|
| L-2-oxothiazolidine-4-carboxylic acid (OTZ) | 5.0 g |
| Dibasic sodium phosphate, anhydrous, United States Pharmacopoeia (USP XXII) | 120 mg |
| Sodium hydroxide, National Formulary (NF) | for pH adj. |
| Water for injection, USP XXII | qs ad |
| pH | 6.5 to 7.0 |
| Osmolarity | 667 mOsmol/L (calc) |
| Na | 321–393 mEq/L |
| HPO$_4$ | 8.4 mEq/L |
| Procysteine ®, 3% injection | |
| L-2-oxothiazolidine-4-carboxylic acid (OTZ) | 3.0 g |
| Dibasic sodium phosphate, anhydrous, United States Pharmacopoeia (USP XXII | 71 mg |
| Sodium hydroxide, National Formulary (NF) | for pH adjustment |
| Water for injection, USP XXII | qs ad |
| pH | 6.5 to 7.0 |
| Osmolarity | 423 mOsmol/L (calc) |
| Na | 193–235 mEq/L |
| HPO$_4$ | 5 mEq/L |

Procysteine® or placebo in capsule form contains the following ingredients:

| Procysteine ®, 250 mg capsule | |
|---|---|
| OTZ | 250 mg |
| Cornstarch, National Formulary (NF) | 167.4 mg |
| Sodium phosphate monobasic fine powder, anhydrous | 150 mg |
| Potassium phosphate monobasic granular | 100 mg |
| Lactose, NF | 64 mg |
| Ascorbic acid, United States Pharmacopoeia (USP) | 3.6 mg |
| Hard, gelatin capsules | |
| Procysteine ®, 500 capsule | |
| OTZ | 500 mg |
| Cornstarch, National Formulary (NF) | 167.4 mg |
| Lactose, NF | 64 mg |
| Ascorbic Acid, United States Pharmacopoeia (USP) | 3.6 mg |
| Hard, gelatin capsules | |
| Placebo, capsule 500 mg | |
| Sodium phosphate monobasic fine powder, anhydrous | 300 mg |
| Potassium phosphate monobasic granular | 200 mg |
| Cornstarch, National Formulary (NF) | 167.4 mg |
| Lactose, NF | 64 mg |
| Ascorbic acid (USP) | 3.6 mg |
| Hard, gelatin capsules | |

4.4. Significance and Rationale

Despite recent critical advances in understanding the pathogenesis of ALS, this remains an untreatable disease. If the primary pathogenic mechanism for motor neuron death in FALS and perhaps in sporadic ALS is cytotoxicity mediated by reactive oxygen species, then therapies directed toward attenuating this toxicity might ameliorate the progression of the disease. In addition, given the possible interplay between oxidative injury and excitotoxic damage to motor neurons, combination trials of anti-oxidants and anti-glutamatergic agents are warranted. Any compound proven to slow the course of the illness will be of immediate importance both clinically and from the perspective of understanding the underlying biology of motor neuron diseases.

The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims.

All publications cited herein are incorporated by reference in their entirety.

5. EXPERIMENTAL SECTION

As discussed above, there is no known cure for ALS. However, Riluzole, a drug that inhibits release of glutamates at pre-synaptic terminals was reported in two controlled studies to extend survival in ALS, although without a concomitant improvement in strength (G Bensimon et al., 1994). The lack of improvement in strength may be secondary to use of an insensitive testing method (Manual Motor Testing) or from a real lack of effect on muscle strength. Riluzole is approved for use in ALS.

It has recently been shown that in transgenic mice which overexpress the mutant SOD1 protein, treatment with high doses of vitamin E and selenium delays onset of disease symptoms. Treatment with Riluzole led to a small (11%), but statistically significant prolongation of survival in the transgenic SOD1 mutant mice.

5.1. Example 1

Procysteine (L-2-Oxothiazolidine-4-Carboxlyic Acid (OTZ)

OTZ is a cysteine prodrug which increases intracellular glutathione levels in animal models (J E Mesina et al., 1989, "Administration of L-2-oxothiazolidine-4-carboxylate increases glutathione levels in rat brain," *Brain Res* 478: 181–183; C G Taylor et al., 1992, "Elevation of lung glutathione by oral supplementation of L2-oxothiaxolidine-4-carboxylate protect against oxygen toxicity in protein-energy malnourished rats," *FASEB* 6: 3101–3107; and J M Williamson and A Meister, 1981 "Simulation of hepatic glutathione formation by administration of L-2-oxothiazolidine-4-carboxylate, a 5-oxoprolinase substrate," *Proc Natl Acad Sci* 78: 936–939. The synthesis of glutathione, an endogenous antioxidant, is often limited by the supply of intracellular cysteine, one of the component amino acids of glutathione. OTZ is metabolized to cysteine intracellularly, where glutathione synthesis occurs (J M Williamson, B Boettcher, and A Meister, 1982, "Intracellular cysteine delivery system that protects against toxicity by promoting glutathione synthesis," *Proc Natl Acad Sci* 79: 6246–6249. OTZ is readily absorbed after oral administration and rapidly eliminated from plasma (T½=1–2 hours) after oral or intravenous administration. In pilot clinical studies of the pharmacokinetics, safety, and efficacy, patients infected with HIV were treated with OTZ injection (n=24; doses up to 100 mg/kg twice per week) or OTZ capsules (n=37; doses up to 9 grams/day for 28 days). Some of these patients continued taking OTZ capsules (up to 9 grams/day) for over two years.

5.2. OTZ in ALS Patients: Phase I Trial

Subjects with ALS were enrolled in a tolerability, pharmacokinetics and pharmacodynamics study of OTZ in ALS patients. In this study, glutathione and cysteine levels in whole blood and CSF and OTZ pharmacokinetics were determined in ten to twenty subjects with ALS. Blood was obtained for baseline glutathione and cysteine levels. A spinal catheter was inserted and baseline CSF samples collected for determination of glutathione and cysteine levels. OTZ (90 ml 5% OTZ injection=4500 mg OTZ) was administered by intravenous infusion through a peripheral vein over 60±10 minutes. At various time points after the start of the OTZ infusion, blood and CSF samples were drawn for determination of OTZ and glutathione levels. The following day, subjects started taking OTZ capsules (3000 mg t.i.d.) for 28 days. After 7 and 14 days of treatment with OTZ capsules, blood was drawn for analyses of safety parameters, glutathione, cysteine and OTZ levels. On the last day of the treatment period, blood and CSF samples were drawn for analysis of OTZ, glutathione, and cysteine levels. The study endpoints were tolerability, and pharmacokinetic and pharmacodynamic data. Safety was determined by clinical history and examination, quantitative neuromuscular examination and a panel of safety laboratory tests. Nine subjects completed the study and samples are analyzed. In addition, CSF was drawn from patients without severe neurological disorders and the GSH levels are analyzed and compared to the levels for ALS patients.

5.3. OTZ in ALS Patients: Phase II Trial

A phase II, bi-center, double-blind randomized controlled comparison trial of the efficacy of OTZ and the antiglutamate agent, Riluzole, versus Riluzole alone in slowing of disease progression in patients with ALS (50 at each center) is performed. Patients receive treatment for 9 months. Riluzole is approved for marketing by the FDA. Riluzole is the only agent so far shown to improve survival in ALS and is therefore currently considered the "standard" treatment in clinical trials.

5.4. Randomization

After providing written informed consent, each patient is randomly assigned to one of two treatment groups, OTZ and Riluzole or Riluzole alone. Patients, investigators and the physical therapists administering the motor and respiratory function testing remain blinded to treatment group assignment throughout the study.

5.5. Study Medications

The OTZ and placebo capsules are identical in appearance. Riluzole is administered as tablets obtained from the manufacturer. Riluzole is administered at 50 mg bid to all subjects. The OTZ dose is the same as used in the Phase I study, 3000 mg p.o. t.i.d. However, the final determination of OTZ dose may be modified. Half the subjects receive active OTZ capsules and the other half receive identical appearing placebo capsules.

5.6. Outcome Measure and Patient Selection

The primary outcome measure is change in motor and pulmonary function after 9 months of experimental therapy as tested with the Tufts Quantitative Neuromuscular Exam (FQNE) and FVC. The secondary outcome measure is based upon ALS Functional Rating Scores.

5.7. Criteria

Inclusion criteria:
1. Patients with a clinical diagnosis of definite or probably ALS, either sporadic or familial ALS, as determined by the El Escorial criteria (World Federation Meeting, 1992);
2. Men and women 18 to 75 years of age;
3. Ability to give informed consent;
4. An FVC greater than or equal to 60% predicted;
5. Females of childbearing age using an effective method of birth control (double barrier or oral contraception)

Exclusion criteria:
1. Dependence on artificial ventilation;
2. Presence of other neurodegenerative diseases (i.e., Parkinson's disease, Alzheimer's disease, etc.);
3. Presence of a clinically significant history of unstable medical illness;
4. Use of N-acetylcysteine (Mucormyst), or nondietary cysteine within the four weeks of randomization;
5. Current tobacco use (smoking or chewing) within six weeks of randomization;
6. Pregnant or nursing females;
7. Concomitant use of other investigational drugs within four weeks of randomization;
8. Chronic use of acetaminophen within four weeks of randomization;
9. FVC less than 60% of predicted.

5.8. Study Visits and Procedures

Screening:

The study design and the informed consent procedure are explained to all prospective subjects. An agreement to participate in the study is obtained in writing from each subject before screening evaluations continue. A complete medical history, general physical exam and neurologic exam is performed. Data on age, sex, family history of ALS, medications, date of symptom onset, date of diagnosis, site of onset and other medical illnesses are collected.

Baseline:

Day 1 The following laboratory and clinical tests are performed:
1. Vital signs;
2. Urinalysis;
3. Complete blood cell count
4. Blood Chemistry Panel
5. Glutathione and cysteine whole blood levels
6. TQNE and FVC measurements Treatment period:

The day following the baseline visit, all subjects begin taking Riluzole tablets b.i.d. In addition, subjects begin taking either OTZ or placebo capsules t.i.d. Subjects continue taking the study medication at the same dosage for the duration of the trial.

Visits every month:

The following procedures are performed:

1. A complete history and physical examination
2. Questions regarding potential adverse effects
3. TQNE and FVC measurements
4. Blood Chemistry panel including liver function tests Three and six month visits In addition to the above procedures, the following laboratory tests are performed:

1. Complete blood cell count
2. Whole blood glutathione and cysteine levels
3. Plasma OTZ measurements levels
4. Riluzole blood levels Final study visit:

The following procedures are performed:

1. A complete history and physical examination
2. Questions regarding potential adverse effects
3. TQNE and FVC measurements
4. Urinalysis
5. Complete blood cell count
6. Blood Chemistry panel including liver function tests
7. Whole blood glutathione and cysteine levels
8. Plasma OTZ measurements
9. Riluzole blood level If the results of any of the safety laboratory tests are abnormal, the patient is followed until the test result returns to normal or the etiology of the abnormality is understood.

Post-treatment:

At the completion of 9 months, all patients receive OTZ until results of data analysis are complete. Patients continue to be followed at regular one month intervals while on study medication.

Data analysis:

Analysis of the primary outcome variable:

Analysis is done on an intention to treat basis. The primary analysis tests the difference in average slopes of arm megascores between the OTZ and Riluzole combination and Riluzole alone groups using a two-way ANOVA with treatment and center in the model, with a two-sided alpha=0.05. Each patient randomized to treatment (those having a baseline measure and at least two measures during the drug administration period of the trial) has a linear regression fitted to his/her arm megaslope versus time data. For patients randomized having a baseline measure but no measurement during drug administration, a slope of −1.25 is assumed. This slope represents the average rate of decline based on database 150 patients from the Western ALS group.

Secondary analyses to support the primary results consists of the following:

1. Testing the difference between average slopes of leg pulmonary megascores between the two groups. Patients with no slope estimate are not be included in the sample.
2. Weighting the individual slopes by their variances and by the number of observations contained in the slope estimate and repeating the ANOVA described above.
3. The mega arm score differences between the baseline and final observations for each subject is analyzed using the primary analysis ANOVA model on these change scores. For randomized patients with no post drug administration measures, a −0.65 (mega arm z-score change in 9 months) change score is assumed, (based on Western ALS database).
4. A two-way analysis of variance with interaction term is used to check for center difference for both the placebo and the drug groups as well as treatment by center interaction. In addition, box plots of the slope means and ranges is provided for visual inspection of consistency across centers.

Analysis of the secondary outcome variable:

The secondary outcome measure is the change in the total ALS functional rating score (ALSFRS) from baseline to 9 months. The analysis involves using a two-way ANOVA with treatment and center in the model, with two-sided alpha=0.05.

Sample size and power:

Muscle strength declines over time in ALS patients. The rate of decline is highly variable from person to person, but for most subjects the decline is linear except for the terminal weeks of illness. Data from a database of 150 ALS patients (from the Western ALS study) studied for at least 6 months reveal the following data:

| Megascore | Average slope (per day) | SD slope |
|---|---|---|
| Arm | −0.003308 | 0.003744 |
| Leg | −0.002292 | 0.004460 |
| FVC % | −0.003496 | 0.004914 |

The arm megascore is less variable than the leg and FVC %, megascores and is therefore used to determine sample size. Using the above data, we determined that to detect a 50% decline in slope for arm megascore, with 80% power, at least 88 patients must be recruited. 100 subjects are enrolled, 50 at each of the two sites.

Time frame for study completion:

The total study length is 18 months. There is a one year period for patient accrual with 9 month of follow up per patient.

Risks, Discomforts and Potential Benefits

Risks and discomforts:

The risks of participating in the study are minimal. They include the risks of drawing blood including a slight pain at the site of the needle stick and possibly developing a small bruise at the puncture site.

Only minor adverse experiences have been associated with OTZ, including stomach upset, dizziness, insomnia, nausea, restlessness and headache. The risk of any of these side effects occurring is small; however, should they occur, the dose of medication is reduced or discontinued entirely. However, OTZ is an experimental drug and unexpected side effects may occur.

Known adverse experiences associated with Riluzole therapy include asthenia, fatigue and asymptomatic elevation of liver function tests.

Benefits:

OTZ slows the rate of progression of ALS and that the combination of Riluzole and OTZ is more efficacious than Riluzole alone. This study shows information and data which ultimately could offer benefit to all patients with ALS.

In a similar manner to the OTZ trial, a GSH isopropyl ester hemisulfate, hemihydrate solution is studied by i.v. administration.

What is claimed is:

1. A method for treating a patient having amyotrophic lateral sclerosis which comprises administering to the patient an effective amount of a non-cysteine glutathione precursor so as to increase the intracellular glutathione levels and alleviate a symptom of amyotrophic lateral sclerosis.

2. A method for treating a patient having amyotrophic lateral sclerosis which comprises administering to the patient an effective amount of a glutathione derivative to increase the intracellular glutathione levels and alleviate a symptom of amyotrophic lateral sclerosis.

3. The method of claim 1 or 2 wherein the symptom of amyotrphic lateral sclerosis is muscle degeneration.

4. The method of claim 1 or 2 wherein the administering further comprises administration of a second ALS therapeutic agent.

5. The method of claim 4, wherein the second ALS agent is Riluzole.

6. The method of claim 1 wherein the non-cysteine substrate is a thiazolidine-4-carboxylate analog or a pharmaceutically acceptable salt thereof.

7. The method of claim 6 wherein the non-cysteine substrate is L-2-oxothiazolidine-4-carboxylate, a carboxylate ester or a pharmaceutically acceptable salt thereof.

8. The method of claim 2, wherein the glutathione derivative is a glutathione diester or a pharmaceutically acceptable salt thereof.

9. The method of claim 2, wherein the glutathione derivative is a glutathione dialkylester or a pharmaceutically acceptable salt thereof.

10. The method of claim 2, wherein the glutathione derivative is a glutathione diethylester or a pharmaceutically acceptable salt thereof.

11. The method of claim 2, wherein the glutathione derivative is a glutathione monoester or a pharmaceutically acceptable salt thereof.

12. The method of claim 2, wherein the glutathione derivative is a glutathione monoalkylester or a pharmaceutically acceptable salt thereof.

13. The method of claim 2, wherein the glutathione derivative is a glutathione monoethylester or a pharmaceutically acceptable salt thereof.

14. The method of claim 2 wherein the glutathione derivative is a glutathione isopropyl ester or a pharmaceutically acceptable salt thereof.

15. The method of claim 2, wherein the glutathione derivative is glutathione monoalkylester hydrochloride.

16. The method of claim 2, wherein the glutathione derivative is glutathione monoalkylester hemihydrosulfate.

17. The method of claim 1 or 2, wherein the non-cysteine glutathione precursor or glutathione derivative is administered orally.

18. The method of claim 1 or 2 wherein the non-cysteine glutathione precursor or glutathione derivative is administered intravenously.

19. The method of claim 1 or 2, wherein the non-cysteine glutathione precursor or glutathione derivative is administered parenterally.

20. The method of claim 1 or 2, wherein the non-cysteine glutathione precursor or glutathione derivative is administered enterally.

21. The method of claim 1 or 2, wherein the non-cysteine glutathione precursor or glutathione derivative is administered in a dose of about 100 mg to about 30 g per day.

22. The method of claim 21, wherein the non-cysteine glutathione precursor or glutathione derivative is administered in three divided doses.

* * * * *